United States Patent
Johnson et al.

(10) Patent No.: US 6,366,810 B1
(45) Date of Patent: Apr. 2, 2002

(54) DETERMINISTIC AND JITTER-FREE DUAL-CHAMBER CARDIAC PACEMAKER

(75) Inventors: Sharon Johnson, Lino Lakes; Frank Dropps, Maple Grove; Jean-Cheui Hsung, Shoreview; James Marcotte, Arden Hills, all of MN (US)

(73) Assignee: Angeion Corporation, Minneapolis, MN (US)

( * ) Notice: Subject to any disclaimer, the term of this patent is extended or adjusted under 35 U.S.C. 154(b) by 0 days.

(21) Appl. No.: 09/395,432

(22) Filed: Sep. 14, 1999

Related U.S. Application Data

(60) Provisional application No. 60/100,153, filed on Sep. 14, 1998.

(51) Int. Cl.[7] ................................................. A61N 1/18
(52) U.S. Cl. ............................................................. 607/9
(58) Field of Search .................................. 607/9, 11, 16

(56) References Cited

U.S. PATENT DOCUMENTS

| | | |
|---|---|---|
| 4,421,116 A | 12/1983 | Markowitz |
| 4,429,697 A | 2/1984 | Nappholz et al. |
| 4,452,248 A | 6/1984 | Keller, Jr. |
| 4,788,980 A | 12/1988 | Mann et al. |
| 5,040,534 A | 8/1991 | Mann et al. |
| 5,103,820 A | 4/1992 | Markowitz |
| 5,334,220 A * | 8/1994 | Sholder .......................... 607/9 |
| 5,340,361 A | 8/1994 | Sholder |
| 5,374,280 A | 12/1994 | den Dulk |
| 5,507,782 A | 4/1996 | Kievbal et al. |
| 5,540,725 A | 7/1996 | Bornzin et al. ................. 607/9 |
| 5,540,727 A | 7/1996 | Tockman et al. |
| 5,800,471 A | 9/1998 | Baumann ..................... 607/25 |
| 5,836,989 A * | 11/1998 | Shelton ........................ 607/27 |
| 6,058,326 A * | 5/2000 | Hess et al. ...................... 607/9 |
| 6,112,119 A * | 8/2000 | Schuelke et al. ............... 607/9 |

* cited by examiner

Primary Examiner—Jeffrey R. Jastrzab
Assistant Examiner—Frances P. Oropeza
(74) Attorney, Agent, or Firm—Patterson, Thuente, Skaar & Christensen, P.A.

(57) ABSTRACT

A deterministic and jitter-free dual chamber brady pacemaker utilizes both a programmed microprocessor and a hardware state machine, both of which are coupled to a real time clock (RTC), random access memory (RAM) and a common escape interval timer. Time of occurrence (TOC) data representative of the time and nature of atrial and ventricular sensed events and pacing events is stored in the RAM. Escape interval periods are timed by the escape interval timer. The microprocessor is operable in both an active mode and an inactive mode without interrupts. In response to the receipt of wakeup commands, the microprocessor operates in the active mode and uses the TOC data from the RAM to reset the escape interval timer to a desired next event interval. The hardware state machine uses the common escape interval timer for timing timeout events and atrial and ventricular sensed events such that pacing pulses are delivered in a determinate manner.

30 Claims, 8 Drawing Sheets

DETERMINISTIC AND JITTER-FREE DUAL-CHAMBER CARDIAC PACEMAKER

REFERENCE TO RELATED APPLICATION

This application claims the benefit of U.S. Provisional Application Ser. No. 60/100,153 filed on Sep. 14, 1998.

BACKGROUND OF THE INVENTION

1. Field of the Invention

The present invention relates generally to cardiac pacemakers. In particular, the present invention is a dual chamber pacemaker having a control system including a programmable microprocessor and a hardware state machine which operate independently and in synchronization with one another.

2. Description of the Related Art

Dual chamber cardiac pacemakers are in widespread use and disclosed generally in the following U.S. Patents:

| Inventor | U.S. Pat. No. |
| --- | --- |
| Markowitz | 4,421,116 |
| Nappholz et al. | 4,429,697 |
| Keller, Jr. | 4,452,248 |
| Markowitz | 5,103,820 |
| Sholder | 5,340,361 |
| den Dulk | 5,374,280 |
| van Krieken et al. | 5,391,189 |
| Kieval et al. | 5,507,782 |
| Tockman et al. | 5,540,727 |

Dual chamber brady (bradycardia) pacemakers have the ability to sense and pace both the atrium and ventricle of the patient's heart. Accordingly, sensed events (i.e., cardiac-induced electrical stimuli) are monitored during both the sequential and repeating atrial and ventricular cardiac cycles. Pacing pulses (i.e., a paced event) can be generated at the end of each cardiac cycle. Whether or not a pacing pulse is generated during each cycle depends upon a number of factors including whether or not a sensed event occurred during the cycle, and if so, the time within the cycle that the sensed event occurred. The pacemaker includes a control system for monitoring the sensed events and controlling the generation of pacing pulses in accordance with a predetermined operating mode.

Pacemakers of these types are typically configured to operate in one of a variety of modes. Commonly used operating modes include DDD (dual-chamber pacing, dual-chamber sensing, dual mode triggered), DDDR (dual-chamber pacing, dual-chamber sensing, dual mode triggered, rate-responsive), DDI (dual-chamber pacing, dual-chamber sensing, dual mode inhibited), and DDIR (dual-chamber pacing, dual-chamber sensing, dual mode inhibited, rate-responsive).

When operating in most, if not all of these dual chamber modes, the control system will make use of time periods known as the atrioventricular interval (AVI) and the ventriculoatrial interval (VAI). Briefly, the AVI is a programmed value representing the desired longest interval from a paced or sensed atrial cycle event to the next paced or sensed ventricular event. In other words, if a sensed ventricular event is not detected within the AVI following the beginning of an atrial cycle, a ventricular pacing pulse will be produced at the expiration of the AVI. Similarly, the VAI is a programmed value representing the desired longest interval from a paced or sensed ventricular cycle event to the next paced or sensed atrial event. If a sensed atrial event is not detected within the VAI following the beginning of a ventricular cycle, an atrial pacing pulse will be produced at the expiration of the VAI.

Electronic control systems for dual chamber pacemakers are described in the above-identified patents as well as in Chapter 10, *Design of Cardiac Pacemakers*. In general, the control systems of dual chamber pacemakers are implemented by using programmed microprocessors and/or hardware logic circuits (also known as state machines). Pacemakers with microprocessor-based control systems are flexible in that they can be programmed to operate in a number of different modes. The selected operational mode can also be quickly and easily changed. In view of the nature of the software design process, microprocessor-based control systems also can be relatively efficiently designed and implemented. However, they consume relatively large amounts of power, thereby limiting the implanted device lifetime. Relatively small but undeterminable latencies (delays) in the program code execution are also inherent in microprocessor-based control systems. Because of these inherent delays, the initiation of pacing pulses and other responses by the pacemaker to sensed cardiac events and timed intervals can be either premature or latent. The result this random indeterminacy of exactly when the pacing pulses will be delivered from a microprocessor-based pacemaker is commonly referred to as jitter.

Hardware state machine control systems generally have lower power requirements than microprocessors and can therefore operate for longer periods of time. Hardware state machine control systems are also relatively deterministic and are not subject to the latencies and jitter problems present in microprocessor-based devices. However, hardware state machine control systems can be relatively inefficient to design and debug. State machine control systems are also relatively inflexible. Unlike microprocessor-based control systems, hardware state machines are generally incapable of operating in different modes or of changing their programmable operation on the fly.

There remains a continuing need for improved pacemaker control systems. In particular, there is a need for a relatively deterministic and jitter-free pacemaker that can be efficiently designed and implemented. A control system of this type which is capable of operating in different modes and capable of having its operation changed on the fly would be especially desirable. Commercial viability would be enhanced if the control system had relatively low power requirements.

SUMMARY OF THE INVENTION

The present invention is a deterministic and jitter-free dual chamber medical device such as a brady pacemaker which can be efficiently designed and implemented. The control system of the pacemaker can be programmed to operate in a number of different operating modes, and is capable of dynamically adapting to changing situations.

In one embodiment, the device includes at least one sense terminal for receiving signals representative of atrial and ventricular sensed events, and pacing circuitry for generating atrial and ventricular pacing pulses in response to pacing commands. The device also includes a common memory for storing data representative of atrial and ventricular events, at least one common timer, a hardware state machine and a programmed microprocessor. The hardware state machine is connected to the at least one sense terminal, the pacing circuitry, the at least one common memory and the common timer. The state machine generates the pacing commands in response to timeouts of the at least one common timer and causes data representative of atrial and ventricular sensed events and atrial and ventricular paced events associated with the pacing commands to be stored in the common memory. The microprocessor is connected to the common memory and the at least one common timer. The microprocessor evaluates the atrial and ventricular events stored in the common memory and loads the at least one common timer with escape interval values representative of a period during which a next pacing event is expected to occur.

One embodiment of the device includes a single common common timer. Also included in this embodiment is a chamber memory location in the common memory for storing data representative of a chamber in which the next pacing event is expected to occur. The microprocessor causes data representative of the chamber in which the next pacing event is expected to occur to be stored in the chamber memory location.

Another embodiment of the device includes an atrial timer for timing atrial events and a separate ventricular timer for timing ventricular events. The hardware state machine generates atrial pacing commands in response to timeouts of the atrial timer and ventricular pacing commands in response to timeouts of the ventricular timer. An advantage of the dual-timer embodiment is that the timer for the chamber that is not expected to have the next sensed event can serve as a trigger to perform a mode switching function for the device.

Yet another embodiment includes a real time clock connected to the microprocessor. The hardware state machine causes time of occurrence data representative of the time of atrial and ventricular sensed events and paced events to be stored in the common memory. The microprocessor determines the escape interval values as a function of the time of occurrence of the atrial and ventricular sensed events and a delay period between the time of occurrence and a then-current time, to compensate for microprocessor-induced latencies.

In another embodiment the microprocessor is programmed to operate in an active mode and load the at least one common timer with the escape interval values in response to wakeup commands, and to operate in an inactive mode after loading the at least one common timer. The hardware state machine issues wakeup commands to the microprocessor in response to timeouts of the at least one common timer and in response to sensed atrial and ventricular events.

DETAILED DESCRIPTION OF THE PREFERRED EMBODIMENTS

Figure 1:
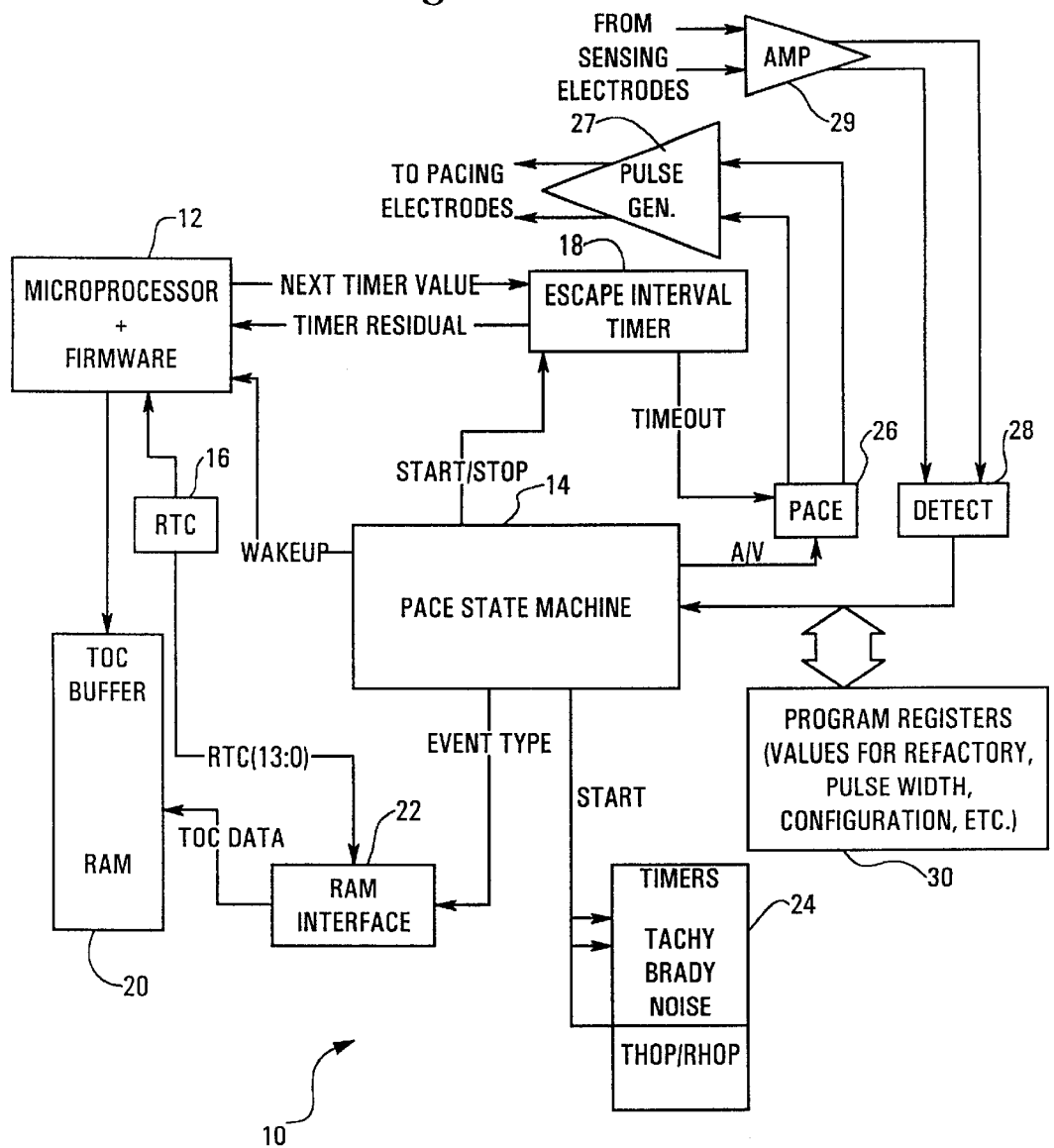
FIG. 1 is a functional block diagram of a dual chamber pacemaker with one common timer in accordance with a first embodiment of the present invention.

An implantable, dual chamber brady (bradycardia) cardiac pacemaker 10 in accordance with a first embodiment of the present invention is illustrated generally in FIG. 1. As shown, pacemaker 10 includes a programmable microprocessor 12 (with associated firmware, not separately shown) and a hardware state machine 14. Both the microprocessor 12 and state machine 14 are interconnected to a real time clock 16, escape interval timer 18 and random access memory (RAM) 20. A RAM interface 22 couples the state machine 14 to RAM 20. Escape interval timer 18 and RAM 20 are in effect common to (i.e., control and/or are controlled by) both microprocessor 12 and state machine 14. State machine 14 is coupled to atrial and ventricular pacing electrodes (not shown) through digital pacing circuit 26 and pulse generator 27. Atrial and ventricular sensing electrodes (not shown) are coupled to state machine 14 through amplifier 29 and detection circuit 28. The state machine 14 is also connected to programmable timers 24. In a preferred embodiment of pacemaker 10, the state machine 14, escape interval timer 18, RAM interface 22, timers 24, pacing circuit 26 and detection circuit 28 are implemented as hardware components in a digital ASIC (application specific integrated circuit). The state machine 14 is configured as a conventional 3-bit Moore model in one embodiment.

The ASIC of pacemaker 10 also includes programmable registers 30 which are coupled to the state machine 14, escape interval timer 18, pacing circuit 26, detection circuit 28 and timers 24. As described in greater detail below, bits in control registers 30 are used by microprocessor 12 and state machine 14 to establish and control the overall operational mode of the pacemaker 10. Other bits in registers 30 are used by the microprocessor 12 and state machine 14 to synchronize and control the operational states of the microprocessor and state machine. Conventional brady pacemaker parameters such as blanking and refractory periods, threshold values and pulse widths used by microprocessor 12 and by the state machine 14 and its associated hardware (i.e., ASIC) components also are stored in registers 30. For example, the brady pacer 10 described herein makes use of a number of conventional and known timing periods including a sense blanking period, a brady refractory period and desired atrial and ventricular escape interval periods. Values for these time periods can be stored in register 30. Embodiments of detection circuit 28 can use automatic threshold control (ATC) approaches such as those described in the Perttu et al. U.S. Pat. No. 5,709,215. Threshold levels and decay constants used by an ATC-type detection circuit can be stored in registers 30. Alternatively, detection circuit 28 can use automatic gain control (AGC) approaches.

Atrial and ventricular pacing pulses are generated by pulse generator 27. Pacing circuit 26 initiates the generation of these pacing pulses in response to the receipt of timeout pacing commands from escape interval timer 18. The type of pacing pulse initiated by circuit 26 (i.e., whether an atrial or ventricular pacing pulse is produced) is controlled by information received from state machine 14. The initiation of a pacing pulse by circuit 26 is referred to as a "pacing event" in this description. Detection circuit 28 processes the electrical signals received from amplifier 29 to detect the occurrence of atrial and ventricular electrical stimuli produced by the heart (not shown) of the patient in which pacemaker 10 is implanted. Atrial and ventricular signals produced by the heart and identified by detection circuit 28 are referred to as "sensed events" in this description. Information representative of atrial and ventricular sensed events is provided to the state machine 14 by detection circuit 28.

Figure 2:
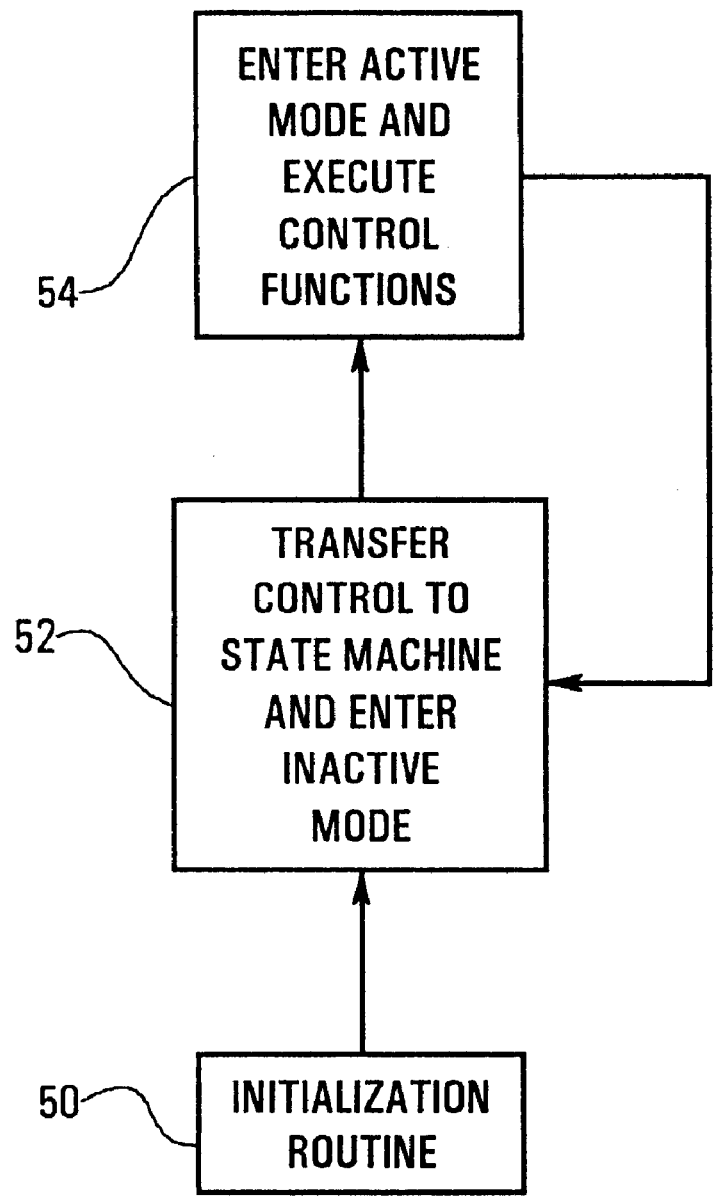
FIG. 2 is a flowchart illustrating the overall operation of the microprocessor shown in FIG. 1.

Overall and high-level operations of pacemaker 10 are controlled through software executed by microprocessor 10 and can be described generally with reference to FIG. 2. Upon the initial application of power to pacemaker 10, microprocessor 12 executes an initialization routine 50 to load the executable control software into RAM 20 and configure the registers 30. Microprocessor 12 also sets state machine 14 to a $\mu$P Wait state 60 (described below with reference to FIG. 3) during the initialization routine 50. When the initialization routine 50 is completed, microprocessor 12 transfers control of pacemaker 10 to state machine 14 by setting and clearing a suspend bit in the registers 30 before entering an inactive mode 52. No pacing-specific control operations are performed by the microprocessor 12 when it is in the inactive mode 52.

As described below with reference to FIG. 3, state machine 14 will in the course of its operation enter a Wakeup state and issue a wakeup command to the microprocessor 12. In response to receipt of the wakeup command, microprocessor 12 enters an active mode 54 and executes its control functions. As described in greater detail below, these control functions include loading escape interval timer 18 with the escape interval time period appropriate for the next cardiac cycle to be monitored and controlled. During the time period that microprocessor 12 is active and executing its programmed algorithm, the suspend bit is set to "1," causing the state machine 14 to remain in the $\mu$P Wait state 60. Upon completion of its control functions, the microprocessor 12 will again transfer control to state machine 14 and enter its inactive mode. Microprocessor 12 repeats the operations of inactive mode 52 and active mode 54 during each consecutive cardiac cycle in response to the wakeup commands received from state machine 14.

Figure 3:
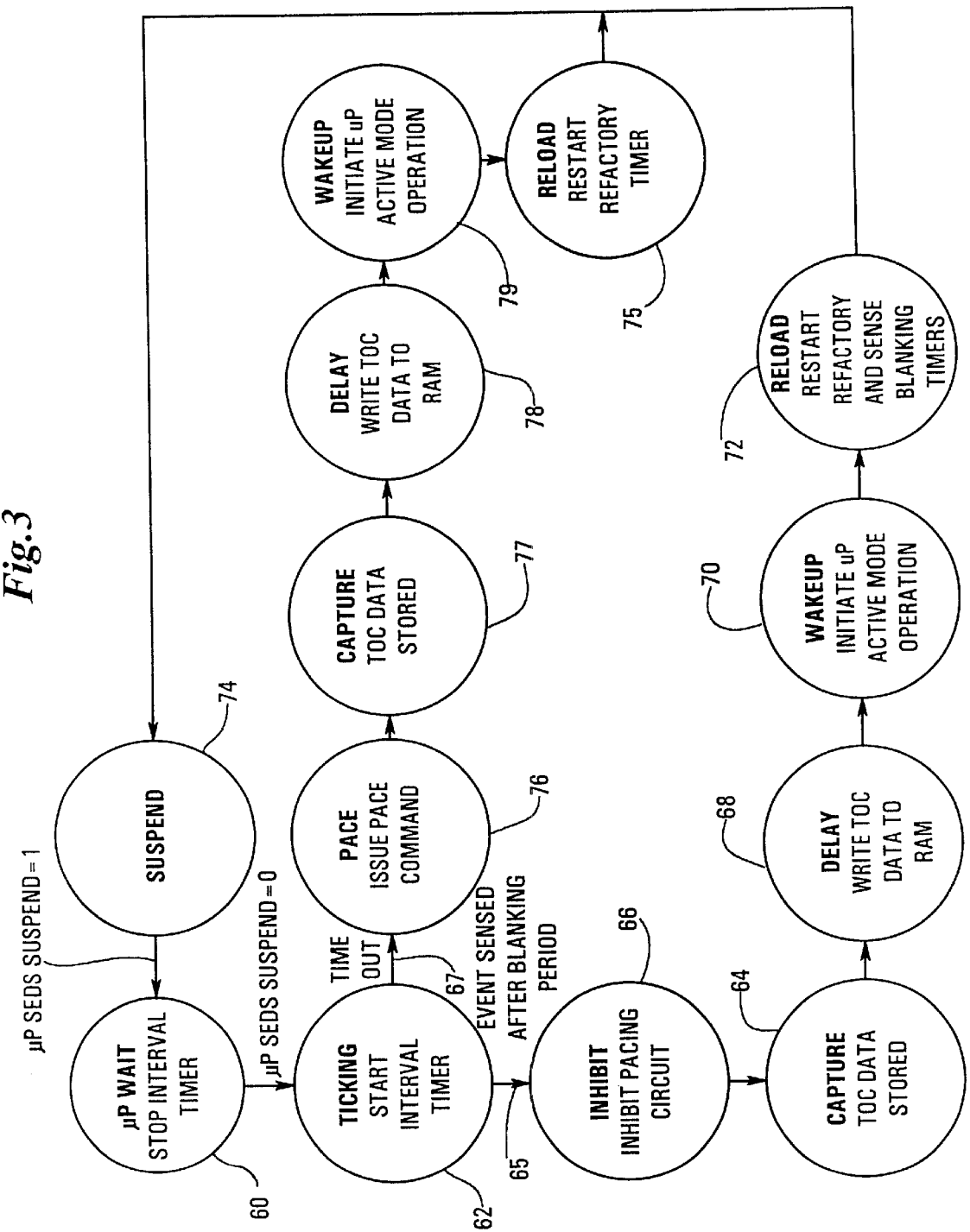
FIG. 3 is a state diagram illustrating the operation of the state machine shown in FIG. 1.

FIG. 3 is a state diagram illustrating in detail the operation of state machine 14. State machine 14 begins monitoring and controlling a then-current cardiac cycle by entering the Ticking state 62 from the $\mu$P Wait state 60 when the microprocessor 12 clears the suspend bit to "0." Upon entering the Ticking state 62, state machine 14 enables (starts) the escape interval timer 18. As described below escape interval timer 18 will have been loaded with an escape interval time period appropriate for the current cardiac cycle while state machine 14 was in the $\mu$P Wait state 60. Escape interval timer 18 is clocked at a 1 KHz rate in one embodiment of the invention. State machine 14 also enables timers 24 to begin timing the sense blanking period, brady refractory period, and any other time periods utilized for control purposes in the particular pacing mode of operation for which the pacemaker 10 is configured. While in the Ticking state 62, state machine 14 effectively awaits the detection of an atrial or ventricular sensed event by detection circuit 28 while the interval timer 18 times the loaded escape interval time period. From the Ticking state 62 state machine 14 will switch to its next state upon the first to occur of either of two events: 1) when an atrial or ventricular sensed event is detected after a sense blanking period (flow path 65), or 2) when the escape interval timer 18 times out (i.e., no sensed event is detected during the escape interval) (flow path 67).

State machine 14 switches to its Inhibit state 66 when an atrial or ventricular sensed event is identified after the sense blanking period. Since the heart effectively performed the needed electrical stimuli on its own under these circumstances, no pacing pulse need be delivered by the pacemaker 10 during this portion of the cardiac cycle. However, escape interval timer 18 is still timing the loaded escape interval time period. In the Inhibit state 66 the state machine 14 therefore inhibits the operation of the pacing circuit 26 for the current cardiac cycle to prevent a timeout of escape interval timer 18 from initiating a pacing pulse. After completing the action of Inhibit state 66 the state machine 14 switches to Capture state 64.

Upon entering the Capture state 64, the state machine 14 causes time of occurrence (TOC) data associated with the sensed event that initiated the state change to be stored in RAM interface 22. State machine 14 then sets a TOC pending bit in registers 30 to indicate to the arbiter of RAM 20 (not separately shown) that TOC data is available. The TOC data that is stored during this operation is the time (from real time clock 16) that the sensed event occurred, and the nature of the event (i.e., whether an atrial sensed event or a ventricular sensed event). In one embodiment, the TOC data is formed and stored by concatenation of the register of real time clock 16 with a 2-bit event code representative of the nature of the event.

After completing its activity in the Capture state 64, state machine 14 switches to the Delay state 68. In the Delay state 68, state machine 14 causes the TOC data stored in interface 22 to be written to RAM 20. The TOC pending bit in registers 30 indicating the presence of TOC data in interface 22 is then cleared by the RAM 20 arbiter to indicate the successful completion of this task.

After the TOC pending bit is cleared, state machine 14 switches to the Wakeup state 70. In the Wakeup state 70, state machine 14 will issue a wakeup command to microprocessor 12 to initiate the active mode operation of the microprocessor. State machine 14 then switches to a Reload state 72 during which the sense blanking period and the brady refractory period (for sensed events) are reloaded into timer 24, and the timer 24 is restarted. After completing the action of Reload state 72, state machine 14 switches to its Suspend state 74.

In the Suspend state 74, state machine 14 is effectively inactive, waiting for the microprocessor 12 to acknowledge the completion of the previous cardiac cycle. This acknowledgement is received by the state machine 14 when the suspend bit in the registers 30 is set to "1." When the suspend bit is set to "1," state machine 14 completes its state cycle by switching back to the $\mu$P Wait state 60. The escape interval timer 18 is disabled (stopped) by the state machine 14 when the machine is in its $\mu$P Wait state 60.

Pace state 76 is entered by state machine 14 if a timeout of escape interval timer 18 occurred while the state machine was in the Ticking state 62. Pacing circuit 26 initiates the generation of an atrial or ventricular pacing pulse when the state machine 14 enters the pacing state 76. The pacing pulse is effectively initiated immediately upon the time out of the escape interval time period. In the embodiment of the pacemaker 10 shown in FIG. 1, the pacing command is generated by the escape interval timer 18. However, in other embodiments (not shown), the pacing command can be generated by the state machine 14 or other hardware components of the ASIC.

After the generation of the pace command in Pace state 76, state machine 14 switches through Capture state 77, Delay state 78 and Wakeup state 79. In the Capture state 77 the state machine 14 causes the TOC data associated with the paced event that initiated the state change to be stored in RAM interface 22. This and other actions performed by state machine 14 in the Capture state 77 are done in a manner similar to those in Capture state 64 described above. The actions performed by state machine 14 in Delay state 78 and Wakeup state 79 also can be done in a manner similar to those in Delay state 68 and Wakeup state 70. From Wakeup state 79 state machine 14 switches to Reload state 75 during which the brady refractory period (for paced events) is reloaded into timer 24, and the timer 24 is restarted. After completing the action of Reload state 75, state machine 14 switches to the Suspend state 74 and performs the above-described action associated with this state.

Figure 4:
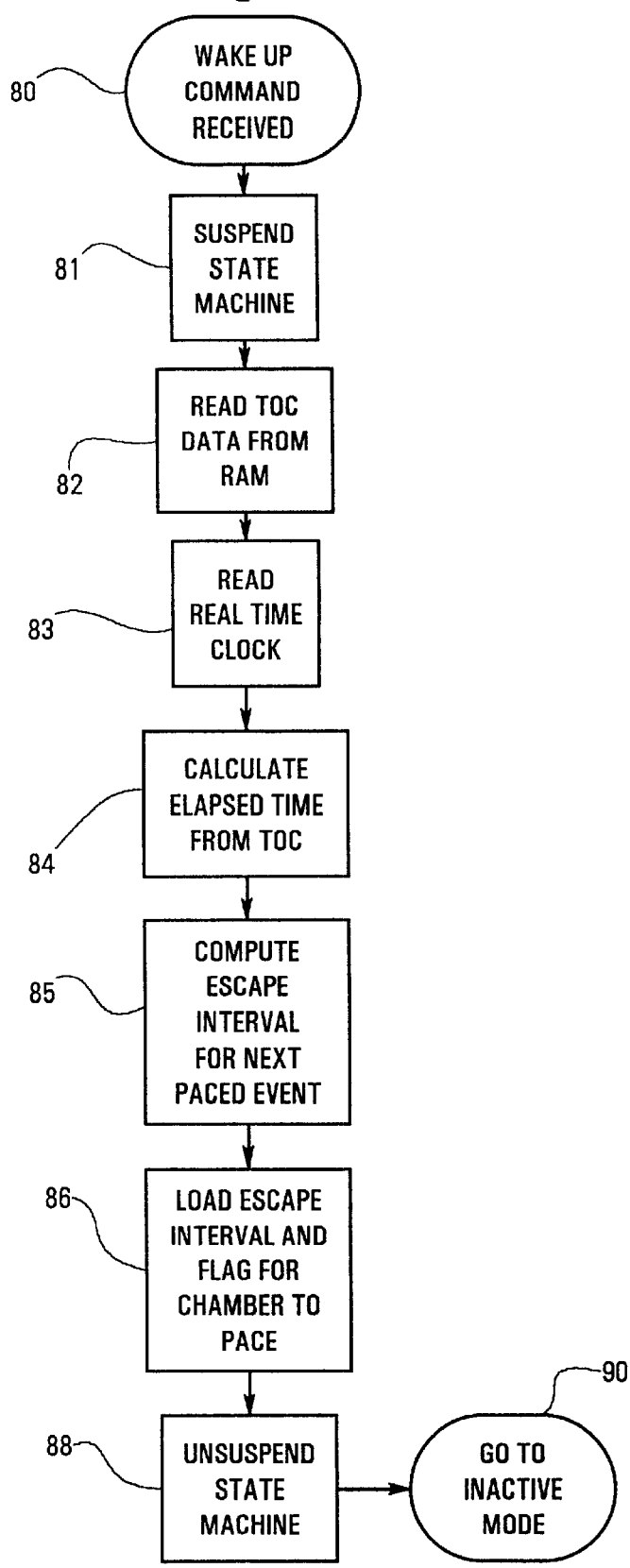
FIG. 4 is a flowchart illustrating the operation of the microprocessor of the pacemaker shown in FIG. 1 when in its active mode shown in FIG. 2.

FIG. 4 is a flow diagram illustrating the control functions performed by microprocessor 12 upon receipt of a wakeup command from state machine 14 (step 80). As indicated by step 81, microprocessor 12 first suspends the operation of state machine 14 by setting the suspend bit to "1." This action effectively provides the state machine 14 with an acknowledgment that the current cardiac cycle is complete. As described above, this acknowledgment causes the state machine 14 to switch from its Suspend state 70 to the $\mu$P Wait state 60, and thereby disable the escape interval timer 18.

Before causing the state machine 14 to begin monitoring and controlling the next subsequent cardiac cycle, microprocessor 12 determines or computes the next value of the escape interval timer 18. The escape interval value loaded into the timer 18 is computed to take into account the delays inherent in the operation of microprocessor 12 during its active mode 54 so the next escape interval will time out at the desired or predetermined length of time following the paced or sensed event of the current cardiac cycle. In other words, the desired value of the escape intervals stored in the registers 30 are adjusted to compensate for latency in the operation of the microprocessor 12 before being loaded into the escape interval timer 18.

As indicated by step 82, the microprocessor begins this process by accessing the TOC data stored in RAM 20 to determine the nature and time of the event that occurred during the current cardiac cycle to initiate operation in the active mode 54. The real time clock 16 is then read by the microprocessor at step 83. From these two time values microprocessor 12 computes the delay period between the current cycle event and the current time (step 84). This delay period can then be subtracted from the stored desired value to compute the escape interval period of the next cardiac cycle (step 85). After being computed in this manner, the next escape interval time period and a flag for the chamber of the heart with which the escape interval is associated are loaded into the registers 30 by the microprocessor 12 as shown at step 86. Although not shown in FIG. 4, when sensed events are identified that occurred within the brady refractory period, microprocessor 12 reads the residual or remaining time on escape interval timer 18, and loads this time value in the escape interval timer as the next escape interval time period.

After reloading the escape interval timer 18, microprocessor 12 effectively returns control of the pacemaker 10 to state machine 14 by clearing the suspend bit to "0" (step 88). State machine 14 then switches to its Ticking state 62 and repeats the monitoring and control operations described above with reference to FIG. 3 for the next cardiac cycle. As indicated by step 90, microprocessor 12 also returns to its inactive mode 52 (FIG. 2) following this action.

Unlike existing microprocessor-controlled pacemakers which allow interrupts to their operation that can affect the timing and order of processing of loading of timer values, the present invention generally does not allow for interrupts and instead uses a wake-up processor with corresponding flag bits to initiate and control software flow within the microprocessor 12. Although external interrupts and most internal operational interrupts are disabled, it will be understood that certain internal operational interrupts (such as device failure or software execution of a safety trap) will remain enabled to allow for recovery from microprocessor hardware and software errors. In addition, interrupts associated with external telecommunications and the like may be enabled to respond to time critical matters having required responses less than 2 milliseconds. In one embodiment, state machine 14 includes a wake-up processor (not separately shown) for generating the wakeup commands during states 70 and 79. The wakeup commands are provided to the microprocessor 12 in the form of interrupts. Events which initiate the generation of wakeup commands are categorized into one of three different priority interrupt categories: 1) maskable XIRQ, 2) non-maskable IRQ, and 3) maskable IRQ. Events within each interrupt category are also assigned relative orders of priority.

In one embodiment of the invention, maskable XIRQ wakeup command interrupts include, in descending order of priority, EGRAM Buffer Full, Real Time Data Byte Reception and High Resolution Timer Timeout. XIRQ wakeup command interrupts are allowed to interrupt an active IRQ wakeup command. Non-maskable IRQ wakeup command interrupts include, in descending order of priority, telemetry activities and charging status information. The maskable IRQ wakeup commands include, in descending order of priority, Atrial Paced Event, Ventricular Paced Event, Atrial Sensed Event, Ventricular Sensed Event, timeouts of timers 24 and TOC Data Buffer Full. Upon the occurrence of one or more simultaneous wake-up events, the wake-up processor will forward to microprocessor 12 an indication of whether it is an IRQ or XIRQ wakeup command. Microprocessor 12 then maintains a record of active wakeup commands, and generally processes these commands in order of relative priority.

Figure 5:
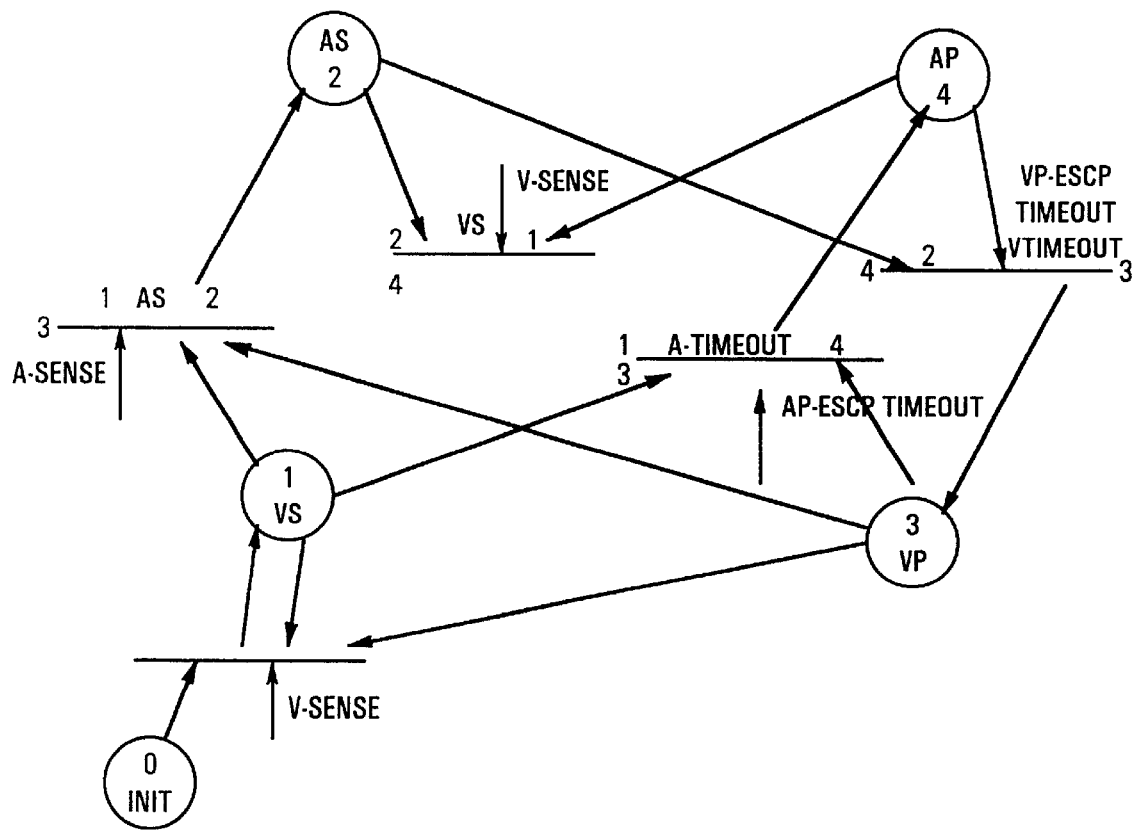
FIG. 5 is a detailed state diagram illustrating the operation of the state machine of the pacemaker shown in FIG. 1 when in a DDD operating mode.

FIG. 5 is a state diagram which illustrates the operation of state machine 14 in a DDD operating mode. In FIG. 5, the states represent periods of time both the microprocessor 12 and state machine 14 are in an inactive state. The bars represent transitions, where both microprocessor 12 and state machine 14, including the wake-up processor, are active. The source states are on the left side of the bars and the destination state is on the right side of the bar. The events which cause the transitions are represented by the vertical arrows.

From State 1: Post V-Sense and Set For A Pace

State 1 to State 2 Transition

Caused by a Sensed A event outside PVARP but before pacing escaping timer timed out. The AsV-delay shall be loaded into the escape interval timer for V pace.

State 1 to State 4 Transition

Caused by escape interval timer timed out. The ApV-delay shall be load into the escape interval timer for V pace.

State 1 to State 1 Transition

Caused by V sensed before A-sense (PVC), the PVARP with extension will be reload into the refractory register and the AEI will reload into the escape interval timer for A pace.

From State 2: Post A-Sense and Set for V Pace
State 2 to State 1 Transition
Caused by V-sense before the escape interval timer expired. The AEI will be loaded into the escape interval timer for A pace.
State 2 to State 3 Transition
Caused by escape interval timer timed out, issue the V pace and Load the AEI into the escape interval timer for A pace.

From State 3: Post A Sense and Set for V Pace
State 3 to State 2 Transition
Caused by A-sensing outside PVARP, and before escape interval timer expired. The AsV-delay will be loaded into the escape interval timer for V pace.
State 3 to State 4 Transition
Caused by escape interval timer timed out. The ApV-delay shall be load into the escape interval timer for V pace.
State 3 to State 1 Transition
Caused by V sensed before A-sense (PVC), the PVARP with extension will be reloaded into the refractory register and the AEI will reload into the escape interval timer for A pace.

From State 4: Post A Pace and Set for V Pace
State 4 to State 1 Transition
Caused by V-sense outside post A-pace Ventricular Blanking period, but before the escape interval timer expired. The AEI will be load into the escape interval timer for A-pace.
State 2 to State 3 Transition
Caused by escape interval timer timed out, issue the V pace and Load the AEI into the escape interval timer for A pace.

The embodiment of pacemaker 10 described above is a dual chamber brady pacer. In other embodiments (not shown), the functionality of the pacer 10 described above is incorporated into a device which is also capable of operating in a number of single chamber pacing modes and as an implanted cardioverter defibrillator (ICD). In this embodiment the mode of operation is controlled by the microprocessor. Briefly, when such a device is operated in a single chamber pacing mode, all the pacing functions are performed by hardware with fixed blanking, refractory and escape time intervals. The microprocessor is therefore placed in a sleep mode, and is not responsive to wakeup commands issued by the state machine. When operated as a dual chamber brady pacer with ICD functionality, the device also makes use of absolute refractory periods as well as an abs (absolute) flag in the registers 30. The abs flag is set by state machine 14 if a sensed event occurs during the absolute refractory periods, and is used by the microprocessor in a conventional manner to control the defibrillation functionality of the device.

Pacemaker 10 offers a number of important advantages. The pacemaker is deterministic and jitter-free since the interval between any given sensed or paced event and a next consecutive paced event is positively determined for each cardiac cycle (i.e., there are no early or latent stimuli). This advantage is achieved through the use of an architecture which does not use preemptive interrupts and an algorithm which is not subject to unknown and variable software code execution time cycles inherent in other software-controlled devices. The determinism of pacing pulse delivery can, for example, be made within 2 milliseconds of the escape interval value. The architecture also allows the pacemaker to be efficiently designed. It can also be programmed to operate in any of a number of different operating modes. Its programmable operation can also be changed on the fly, allowing the pacemaker to dynamically adapt to changing situations.

Figure 6:
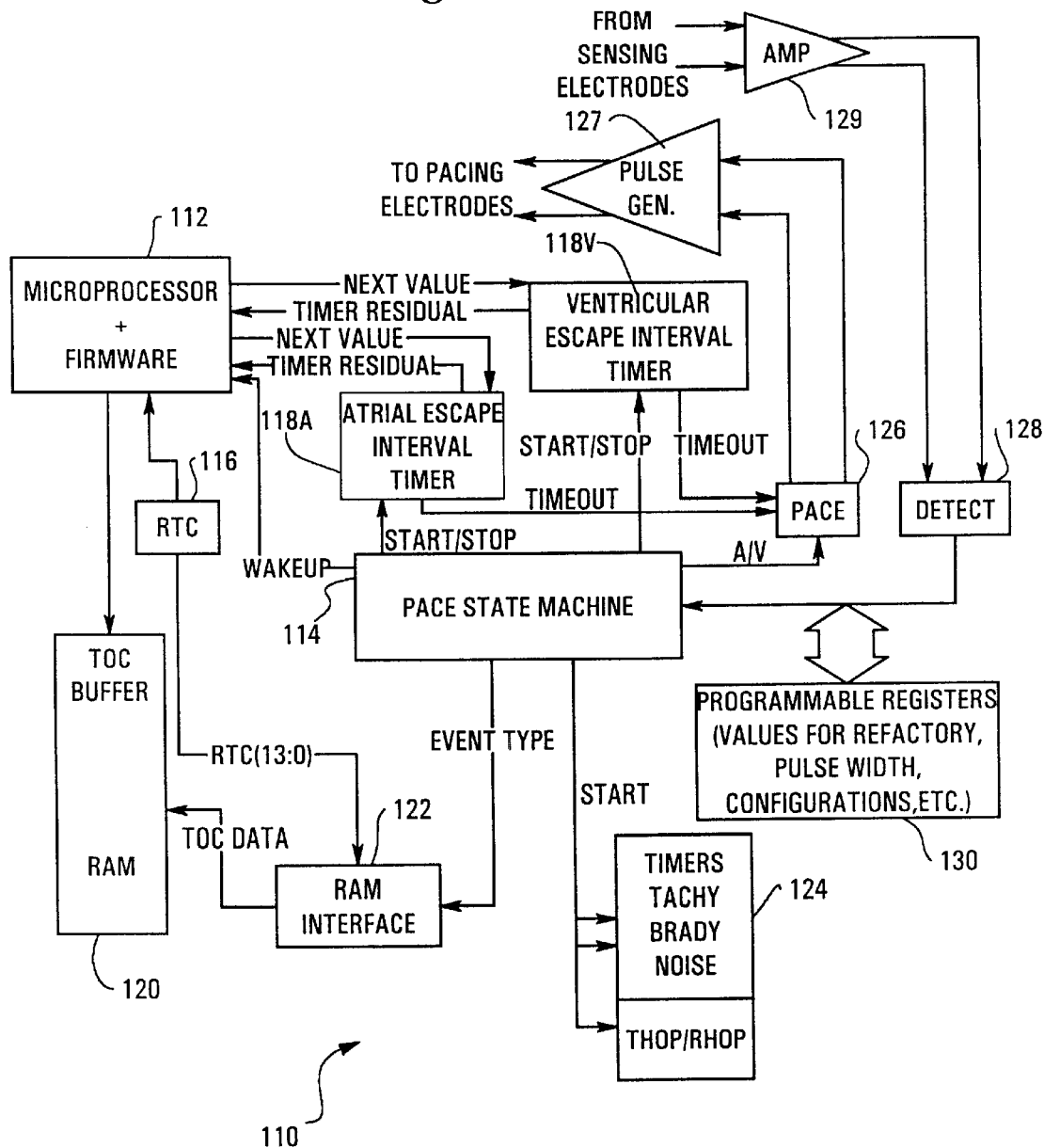
FIG. 6 is a functional block diagram of a dual chamber pacemaker with two common timers in accordance with a second embodiment of the present invention.

An implantable dual chamber brady cardiac pacemaker 110 in accordance with a second embodiment of the present invention is illustrated generally in FIG. 6. Pacemaker 110 is similar in many respects to pacemaker 10 described above, and functionally equivalent components are identified by similar reference numbers. An important feature of pacemaker 110 which is different than pacemaker 10 is its use of plural (two are shown) common timers 118A and 118V. As shown, both timers 118A and 118V are connected to microprocessor 112, state machine 114 and pacing circuit 126. Timers 118A and 118V are dedicated to specific cardiac cycles. In particular, timer 118A times atrial escape intervals for atrial cycle events, while timer 118V times ventricular escape intervals for ventricular cycle events.

Figure 7:
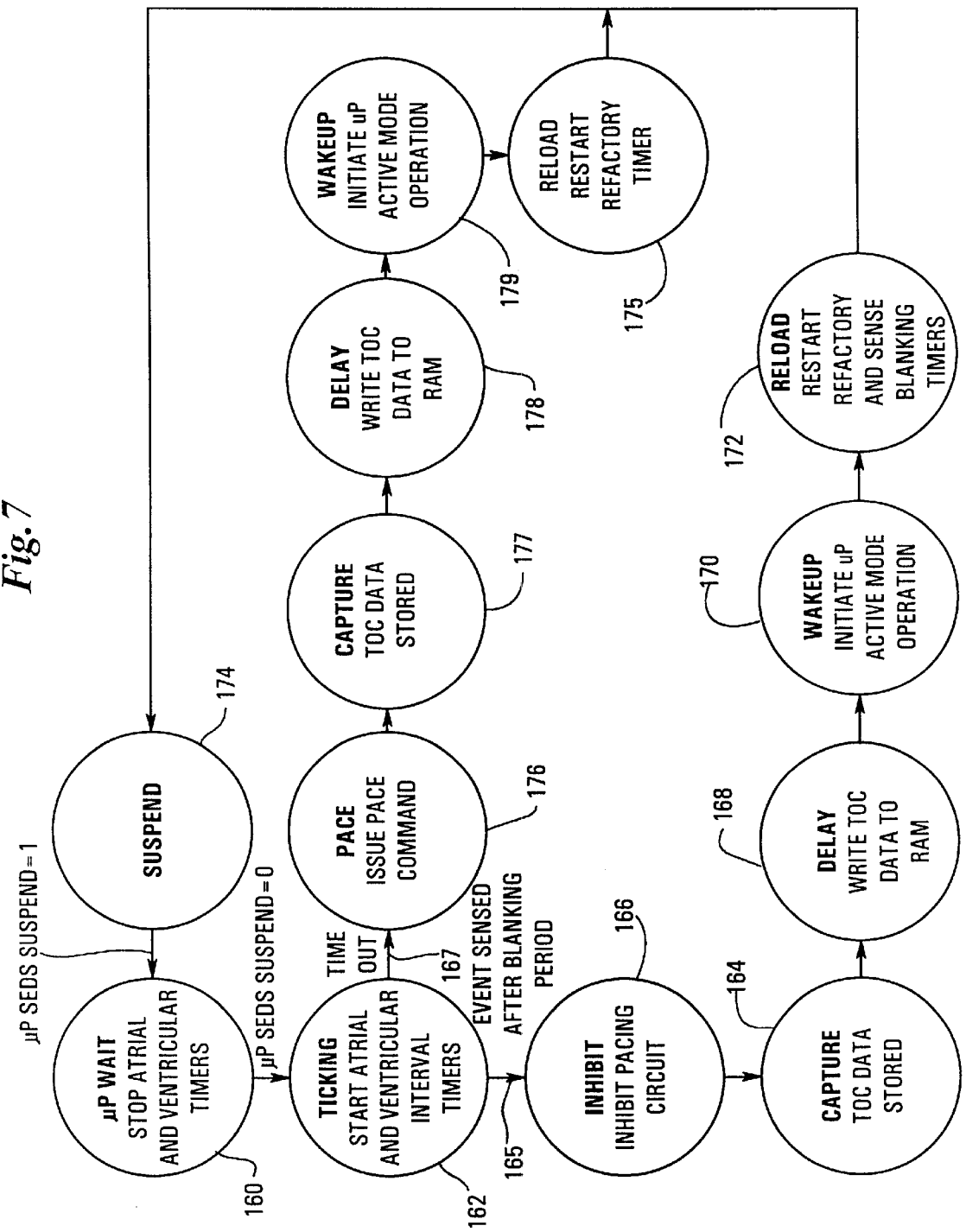
FIG. 7 is a state diagram illustrating the operation of the state machine shown in FIG. 6.

FIG. 7 is a state diagram illustrating in detail the operation of state machine 114. The state machine 114 begins monitoring and controlling a then-current cardiac cycle by entering the Ticking state 162 from the $\mu$P Wait state 160 when the microprocessor 112 clears the suspend bit to "0." Upon entering the Ticking state 162, state machine 114 enables (starts) both the atrial escape interval timer 118A and the ventricular escape interval timer 118V. As described below, the timer associated with the then-current cardiac cycle (i.e. timer 118A if the then-current cycle is an atrial cycle, and timer 118V if a ventricular cycle) will have been loaded with an escape interval time period appropriate for the current cardiac cycle while the state machine 114 was in the $\mu$P Wait state 160. The timer 118A or 118V associated with the other or non-current cardiac cycle can be loaded with a cross-chamber interval value which is longer than the escape interval period of the current cardiac cycle. The timer 118A or 118V associated with the other or non-current cardiac cycle will therefore not time out until after the timer associated with the current cycle times out. State machine 114 also enables timers 124 to begin timing the sense blanking period, brady refractory period and any other time periods utilized for control purposes in the particular pacing mode of operation for which the pacemaker 110 is configured.

While in the Ticking state 162, state machine 114 effectively awaits the detection of a sensed event for the current cardiac cycle by detection circuit 128 while the interval timer 118A or 118V for the current cardiac cycle times the loaded escape interval time period. From the Ticking state 162 state machine 114 will switch to its next state upon the first to occur of either of two events: 1) when a sensed event or the then-current cardiac cycle is detected after a sense blanking period (flow path 165), or 2) when the escape interval timer 118A or 118V associated with the current cardiac cycle times out (i.e., no sensed event is detected during the escape interval) (flow path 167).

State machine 114 switches to its Inhibit state 166 when a sensed event for the current cardiac cycle is identified after the sense blanking period. Since the heart effectively performed the needed electrical stimuli on its own under these circumstances, no pacing pulse need be delivered by the pacemaker 110 during this portion of the cardiac cycle. However, escape interval timers 118A and 118V are still timing the loaded escape interval time periods. In the Inhibit state 166 the state machine 114 therefore inhibits the operation of the pacing circuit 126 for the current cardiac cycle to prevent a timeout of escape interval timer 118A or 118V from initiating a pacing pulse. After completing the action of Inhibit state 166 the state machine 114 switches to Capture state 164.

Upon entering the Capture state 164, the state machine 114 causes the TOC data associated with the sensed event that initiated the state change to be stored in RAM interface 122. State machine 114 then sets a TOC pending bit in registers 130 to indicate to the arbiter of RAM 120 (not separately shown) that TOC data is available. The TOC data that is stored during this operation is the time (from real time clock 116) that the sensed event occurred, and the nature of the event (i.e., whether an atrial sensed event or a ventricular sensed event).

After completing its activity in the Capture state 164, state machine 114 switches to the Delay state 168. In the Delay state 168, state machine 114 causes the TOC data stored in interface 122 to be written to RAM 120. The TOC pending bit in registers 130 indicating the presence of TOC data in interface 122 is then cleared by the RAM 120 arbiter to indicate the successful completion of this task.

After the TOC pending bit is cleared, state machine 114 switches to the Wakeup state 170. In the Wakeup state 170, state machine 114 will issue a wakeup command to microprocessor 112 to initiate the active mode operation of the microprocessor. State machine 114 then switches to a Reload state 172 during which the sense blanking period and the brady refractory period (for sensed events) are reloaded into timer 124, and the timer 124 restarted. After completing the action of Reload state 172, state machine 114 switches to its Suspend state 174.

In the Suspend state 174, state machine 114 is effectively inactive, waiting for the microprocessor 112 to acknowledge the completion of the previous cardiac cycle. This acknowledgement is received by the state machine 114 when the suspend bit in the registers 130 is set to "1." When the suspend bit is set to "1," state machine 114 completes its state cycle by switching back to the μP Wait state 160. Both escape interval timers 118A and 118V are disabled (stopped) by the state machine 114 when the machine is in its μP Wait state 160.

Pace state 176 is entered by state machine 114 if a timeout of escape interval timer 118A or 118V associated with the then-current cardiac cycle occurred while the state machine was in the Ticking state 162. Pacing circuit 126 initiates the generation of an atrial or ventricular pacing pulse (i.e., a pulse for the then-current cardiac cycle) when the state machine 114 enters the pacing state 176. The pacing pulse is effectively initiated immediately upon the timeout of the escape interval time period. In the embodiment of the pacemaker 110 shown in FIG. 6, the pacing command is generated by the escape interval timer 118A or 118V. However, in other embodiments (not shown), the pacing command can be generated by the state machine 114 or other hardware components of the ASIC. Unlike the pacemaker 10 described above in which its state machine 14 determined (e.g., via a flag set in registers 30) and provided to its pacing circuit 26 information representative of the chamber in which the paced event is to occur, pacing circuit 126 of pacemaker 110 effectively receives information representative of the chamber to pace directly from the timer 118A or 118V which timed out and initiated the transition to the Pace state 176.

After the generation of the pace command in Pace state 176, state machine 114 switches through Capture state 177, Delay state 178 and Wakeup state 179. In the Capture state 177 the state machine 114 causes the TOC data associated with the sensed event that initiated the state change to be stored in RAM interface 122. This and other actions performed by state machine 114 in the Capture state 177 are done in a manner similar to those in Capture state 164 described above. The actions performed by state machine 114 in Delay state 178 and Wakeup state 179 also can be done in a manner similar to those in Delay state 168 and Wakeup state 170. From Wakeup state 179 state machine 114 switches to Reload state 175 during which the brady refractory period (for sensed events) is reloaded into timer 124, and the timer restarted. After completing the action of Reload state 175, state machine 114 switches to the Suspend state 174 and performs the above-described actions associated with this state.

State machine 114 includes a wakeup processor (not separately shown) for generating the wakeup commands during states 170 and 179 in a manner similar to that of pacemaker 10 and described above.

Figure 8:
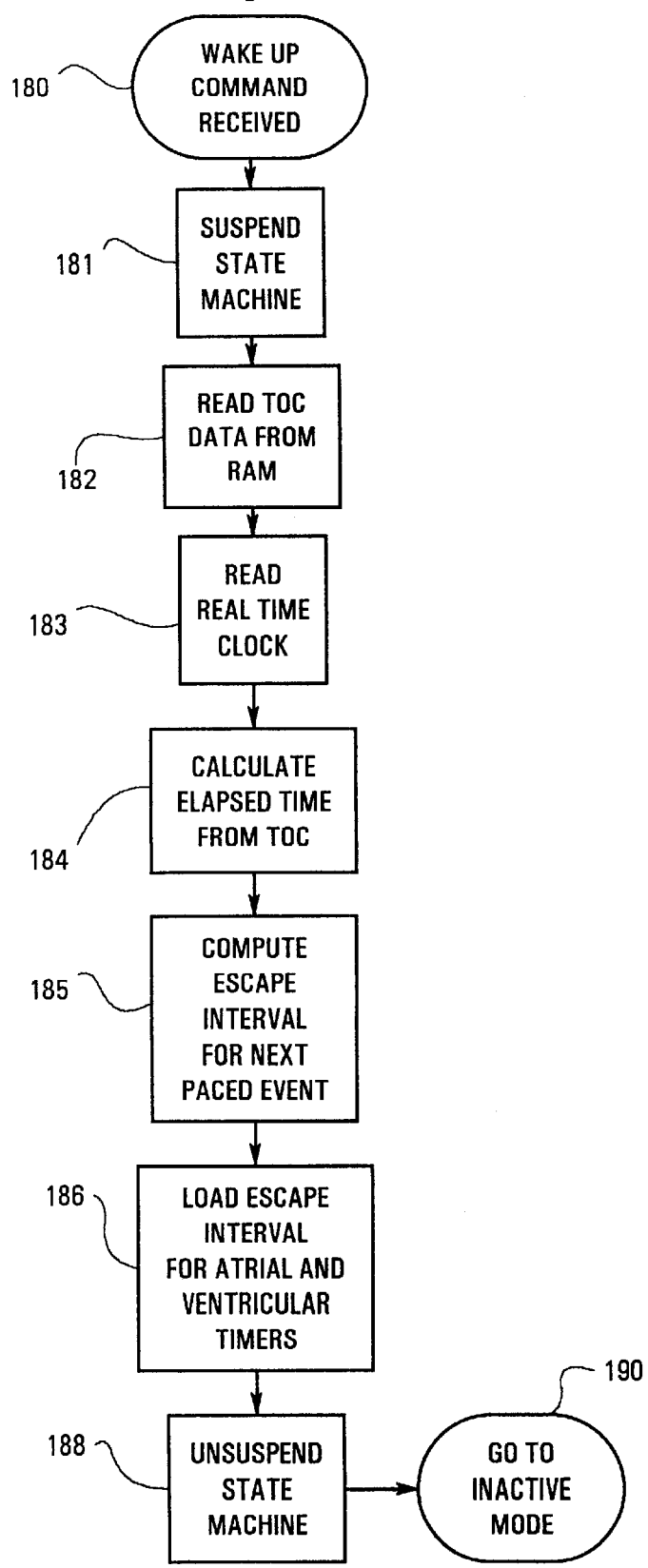
FIG. 8 is a flow chart illustrating the operation of the microprocessor of the pacemaker shown in FIG. 6 when in its active mode.

FIG. 8 is a flow diagram illustrating the control functions performed by microprocessor 112 upon receipt of a wakeup command from state machine 114 (step 180). As indicated by step 181, microprocessor 112 first suspends the operation of state machine 114 by setting the suspend bit to "1." This action effectively provides the state machine 114 with an acknowledgment that the current cardiac cycle is complete. As described above, this acknowledgment causes the state machine 114 to switch from its Suspend state 170 to the μP Wait state 160, and thereby disable the escape interval timers 118A and 118V.

Before causing the state machine 114 to begin monitoring and controlling the next subsequent cardiac cycle, microprocessor 112 determines or computes the next values of the escape interval timers 118A and 118V. The escape interval value loaded into the timer 118A or 118V associated with the next cardiac cycle is computed to take into account the delays inherent in the operation of microprocessor 112 during its active mode so the next escape interval will time out at the desired or predetermined length of time following the paced or sensed event of the current cardiac cycle. In other words, the desired values of the escape intervals stored in the registers 130 are adjusted to compensate for latency in the operation of the microprocessor 112 before being loaded into the escape interval timer 118A or 118V.

As indicated by step 182, the microprocessor 112 begins this process by accessing the TOC data stored in RAM 120 to determine the nature and time of the event that occurred during the current cardiac cycle to initiate operation in the active mode. The real time clock 116 is then read by the microprocessor 112 at step 183. From these two time values microprocessor 112 computes the delay period between the current cycle event and the current time. This delay period can then be subtracted from the stored desired value to compute the escape interval period of the next cardiac cycle (step 185). After being computed in this manner, the escape interval time period for the next cardiac cycle is loaded into the associated timer 118A or 118V by the microprocessor 112 as shown at step 186. The timer 118A or 118V associated with the other or current cardiac cycle can be loaded at step 186 with a cross-chamber interval value which is longer than the escape interval period of the next cardiac cycle. The timer 118A or 118V associated with the other or current cardiac cycle will therefore not time out during the next cardiac cycle until after the timer associated with the next cycle times out. Although not shown in FIG. 8, when sensed events are identified that occurred within the brady refractory period, microprocessor 112 reads the residual or remaining time on the associated escape interval timer 118 A or 118V, and loads this time value in the escape interval timer as the next escape interval time period.

After reloading the escape interval timers 118A and 118V, microprocessor 112 effectively returns control of the pacemaker 110 to state machine 114 by clearing the suspend bit to "0" (step 188). State machine 114 then switches to its Ticking state 162 and repeats the monitoring and control operations described above with reference to FIG. 7 for the next cardiac cycle. As indicated by step 190, microprocessor 12 also returns to its inactive mode following this action.

Like pacemaker 10 described above, pacemaker 110 is deterministic and jitter-free, and capable of programmable operation. An advantage of the dual timer configuration of pacemaker 110 is the relatively efficient software control routines which can be used. These simplified control routines result at least in part from the lack of a need to determine (e.g., by setting a flag) which chamber is associated with the next cardiac cycle. Another advantage is that the timer not being used to time the current cardiac cycle can be used to initiate mode switching operations (the decision making step for changing between single and dual chamber operating modes depending upon the relationship between atrial and ventricular pulses.

Although the present invention has been described with reference to preferred embodiments, those skilled in the art will recognize that changes can be made in form and detail without departing from the spirit and scope of the invention. In particular, the pacemaker can also be configured to operated in any of a variety of dual chamber and other brady pacing modes.

What is claimed is:

1. An implantable medical device for providing dual chamber pacing to a patient's heart, comprising:
    at least one sense terminal that receives signals representative of atrial and ventricular sensed events;
    pacing circuitry that generates atrial and ventricular pacing pulses in response to pacing commands;
    a common memory that stores data representative of atrial and ventricular events;
    at least one common timer;
    a hardware state machine connected to the at least one sense terminal, the pacing circuitry, the common memory and the at least one common timer, that generates the pacing commands in response to timeouts of the at least one common timer and that causes data representative of atrial and ventricular sensed events and atrial and ventricular paced events associated with the pacing commands to be stored in the common memory; and
    a programmed microprocessor connected to the common memory and the at least one common timer, that evaluates the data representative of the atrial and ventricular sensed and pacing events stored in the common memory and loads the at least one common timer with escape interval values representative of a period during which a next pacing event is expected to occur.

2. The medical device of claim 1 wherein:
    the at least one common timer includes a single common timer;
    the common memory includes a chamber memory location that stores data representative of a chamber in which the next pacing event is expected to occur; and
    the microprocessor causes data representative of the chamber in which the next pacing event is expected to occur to be stored in the chamber memory location.

3. The medical device of claim 1 wherein:
    the at least one common timer includes:
        an atrial timer for timing atrial events; and
        a ventricular timer for timing ventricular events; and
    the hardware state machine generates atrial pacing commands in response to timeouts of the atrial timer and ventricular pacing commands in response to timeouts of the ventricular timer.

4. The medical device of claim 3 wherein the microprocessor loads the one of the atrial and ventricular timers associated with a chamber in which the next pacing event is expected to occur with an escape interval value representative of a period during which the next pacing event is expected to occur, and loads the other of the atrial and ventricular timers associated with a chamber in which the next pacing event is not expected to occur with a cross chamber timeout value which is longer than the escape interval value.

5. The medical device of claim 1 wherein:
    the device further includes a real time clock connected to the microprocessor and the hardware state machine;
    the hardware state machine causes time of occurrence data representative of the time of atrial and ventricular sensed events and atrial and ventricular paced events to be stored in the common memory; and
    the microprocessor determines the escape interval values as a function of the time of occurrence data stored in the common memory.

6. The medical device of claim 5 wherein the microprocessor determines the escape interval values as a function of the time of occurrence of the atrial and ventricular sensed events and a delay period between the time of occurrence and a then-current time, to compensate for microprocessor-induced latencies.

7. The medical device of claim 1 wherein:
    the microprocessor is programmed to operate in an active mode and load the at least one common timer with the escape interval values in response to wakeup commands, and to operate in an inactive mode after loading the at least one common timer; and
    the hardware state machine issues wakeup commands to the microprocessor in response to timeouts of the at least one common timer and in response to sensed atrial and ventricular events.

8. The medical device of claim 7 wherein the hardware state machine includes:
    ticking state means for operating in a ticking state and identifying timeouts of the at least one common timer and identifying atrial and ventricular sensed events;
    pace state means for operating in a pace state and issuing pacing commands to the pacing circuitry when timeouts of the at least one common timer are identified;
    capture state means for operating in a capture state and causing the data representative of the atrial and ventricular sensed events and the atrial and ventricular paced events to be stored in the common memory; and
    wakeup state means for operating in a wakeup state and issuing the wakeup commands to the microprocessor when timeouts of the at least one common timer and atrial and ventricular sensed events are identified.

9. The medical device of claim 8 wherein the hardware state machine further includes suspend state means for operating in a suspend state and causing the state machine to be inactive after operation in the wakeup state.

10. The medical device of claim 8 wherein the hardware state machine further includes microprocessor wait state means for operating in a wait state and disabling the at least one common timer after operation in the wakeup state and before operation in the ticking state.

11. The medical device of claim 8 wherein the hardware state machine further includes inhibit state means for operating in an inhibit state and inhibiting operation of the pacing circuitry after atrial and ventricular sensed events are identified during operation in the ticking state.

12. A dual chamber cardiac pacemaker, including:
one or more sense terminals that receives signals representative of atrial and ventricular sensed events;
one or more pulse generators responsive to atrial and ventricular pacing commands that generate atrial and ventricular pacing pulses;
common random access memory that stores data;
at least one common escape interval timer that times escape intervals;
a programmed microprocessor coupled to the random access memory and escape interval timer that is operable without interrupts in an active mode in response to wakeup commands and in an inactive mode and resets the at least one escape interval timer to a desired next pacing event interval; and
a hardware state machine coupled to the sense terminals, pulse generators, random access memory, escape interval timer and microprocessor that issues pacing commands to the pulse generators when timeout events are identified and issues wakeup commands to the microprocessor when timeout events and atrial and ventricular sensed events are identified.

13. The pacemaker of claim 12 further comprising:
a real time clock;
wherein the common random access memory stores time of occurrence data representative of the time of atrial and ventricular sensed events and pacing events;
wherein the programmed microprocessor includes an active mode control means operable when the microprocessor is in the active mode, the active mode control means including:
time of occurrence access means for reading the time of occurrence data from the random access memory;
timer means for resetting the at least one escape interval timer to a desired next pacing event interval as a function of the time of occurrence data read from the memory; and
inactive mode means for causing the microprocessor to operate in the inactive mode after resetting the at least one escape interval timer; and
wherein the hardware state machine includes:
ticking state means for operating in a ticking state and identifying escape interval timer timeout events and atrial and ventricular sensed events;
pace means for operating in a pace state and issuing pacing commands to the pulse generators when timeout events are identified;
capture state means for operating in a capture state and storing time of occurrence data representative of pacing events and identified atrial and ventricular sensed events; and
wakeup state means for operating in a wakeup state and issuing wakeup commands to the microprocessor when timeout events and atrial and ventricular sensed events are identified.

14. The pacemaker of claim 13 wherein the hardware state machine further includes suspend state means for operating in a suspend state and causing the state machine to be inactive after operation in the wakeup state.

15. The pacemaker of claim 13 wherein the hardware state machine further includes microprocessor wait state means for operating in a wait state and disabling the at least one common timer after operation in the wakeup state and before operation in the ticking state.

16. The pacemaker of claim 13 wherein the hardware state machine further includes inhibit state means for operating in an inhibit state and inhibiting operation of the pacing circuitry after atrial and ventricular sensed events are identified during operation in the ticking state.

17. The pacemaker of claim 12 wherein:
the at least one common timer includes a single common timer;
the common memory includes a chamber memory location that stores data representative of a chamber in which the next pacing event is expected to occur; and
the microprocessor causes data representative of the chamber in which the next pacing event is expected to occur to be stored in the chamber memory location.

18. The pacemaker of claim 12 wherein:
the at least one common timer includes:
an atrial timer for timing atrial events; and
a ventricular timer for timing ventricular events; and
the hardware state machine generates atrial pacing commands in response to timeouts of the atrial timer and ventricular pacing commands in response to timeouts of the ventricular timer.

19. The pacemaker of claim 18 wherein the microprocessor loads the one of the atrial and ventricular timers associated with the chamber in which the next pacing event is expected to occur with an escape interval value representative of a period during which the next pacing event is expected to occur, and loads the other of the atrial and ventricular timers associated with the chamber in which the next pacing event is not expected to occur with a cross chamber timeout value which is longer that the escape interval value.

20. A method of operating an implantable medical device for providing dual chamber pacing to a patient's heart, comprising:
(a) storing data representative of atrial and ventricular sensed and paced events in a common memory;
(b) using a programmed microprocessor to evaluate the data in the common memory to determine an escape interval value to be loaded into at least one common timer, the escape interval value representative of a period during which a next pacing event is expected to occur; and
(c) activating a hardware state machine to control the delivery of atrial and ventricular pacing pulses in response to timeouts of the at least one common timer, such that the delivery of pacing pulses is deterministic within 2 milliseconds of the associated escape interval value.

21. The method of claim 20 wherein step (a) includes storing data representative of the time of occurrence of the events.

22. The method of claim 20 wherein step (a) includes storing data representative of the nature of the event.

23. The method of claim 21 wherein step (b) includes using the programmed microprocessor to determine the escape interval value as a function of stored data representative of the time of occurrence of the event and the then-current time to compensate for microprocessor-induced delays.

24. The method of claim 20 wherein step (b) includes operating the microprocessor in an active mode to determine the escape interval value and load the escape interval value into the at least one common timer, and operating the microprocessor in an inactive mode after the escape interval value is loaded into the at least one common timer.

25. The method of claim 20 wherein step (c) includes operating the state machine in a capture state during which the data representative of the paced and sensed events is stored in the common memory.

26. The method of claim 20 wherein step (c) further includes operating the state machine in a ticking state during which timeouts of the common timer and atrial and ventricular sensed events are identified.

27. The method of claim 26 wherein step (c) further includes operating the state machine in a wakeup state during which the microprocessor evaluates the data in the common memory to determine the escape interval value.

28. The method of claim 27 wherein step (c) further includes operating the state machine in a microprocessor wait state during which the common timer is disabled after operation in the wakeup state and before operation in the ticking state.

29. The method of claim 28 wherein step (c) further includes operating the state machine in an inhibit state during which operation of the pacing circuitry is inhibited after atrial and ventricular sensed events are identified during operation in the ticking state.

30. The method of claim 20 wherein step (b) is operable without interrupts in an active mode in response to wakeup commands and in an inactive mode and wherein step (c) issues wakeup commands to the microprocessor when timeout events and atrial and ventricular sensed events are identified.

* * * * *